United States Patent [19]

Saito et al.

[11] Patent Number: 4,970,296

[45] Date of Patent: Nov. 13, 1990

[54] HETERODIMERIC T LYMPHOCYTE RECEPTOR

[75] Inventors: Haruo Saito, Arlington; David M. Kranz, Somerville; Herman N. Eisen, Waban; Susumu Tonegawa, Chestnut Hill, all of Mass.

[73] Assignees: Massachusetts Instiute of Technology, Cambridge, Mass.; Board of Trustees of Leland Stanford Jr. University, Stanford, Calif.

[21] Appl. No.: 385,897

[22] Filed: Jul. 27, 1989

Related U.S. Application Data

[63] Continuation of Ser. No. 666,988, Oct. 31, 1984, Pat. No. 4,873,190, which is a continuation-in-part of Ser. No. 620,122, Jun. 13, 1984, Pat. No. 4,874,845, and a continuation-in-part of Ser. No. 663,809, Oct. 22, 1984, which is a continuation-in-part of Ser. No. 585,333, Mar. 1, 1984, abandoned.

[51] Int. Cl.$^5$ ............... C07K 13/00; C07K 15/00; C12N 15/00
[52] U.S. Cl. .................. 530/323; 530/395; 435/172.3
[58] Field of Search ............... 530/395, 323; 435/172.3

[56] References Cited

U.S. PATENT DOCUMENTS 4,713,332 12/1987 Mak ........................... 435/70

*Primary Examiner*—Thomas D. Mays
*Assistant Examiner*—Richard C. Peet
*Attorney, Agent, or Firm*—Kilpatrick & Cody

[57] ABSTRACT

Disclosed is a heterodimeric T lymphocyte receptor comprising an alpha and a beta subunit. Each subunit consists of a signal peptide, variable, joining, constant, transmembrane, and cytoplasmic regions. The two subunits are connected by a disulfide bond between cysteine residues located between the constant and transmembrane region.

The structure, amino acid, and nucleotide sequence of the lymphocyte receptor were determined using cDNA clones derived from a functional murine cytotoxic T lymphocyte clone. The genes corresponding to these cDNA are expressed and rearranged specifically in T cells and have significant sequence homologies to immunoglobulin V and C genes.

Both the T cell receptor protein and its subunits may be produced from the cDNA clones. The protein molecules may be further used for the production of T-cell clone specific antibodies.

3 Claims, 11 Drawing Sheets

|  |  | 100 |  |  |  |  |  |  | 110 |  |  |
|---|---|---|---|---|---|---|---|---|---|---|---|
| PHDS58 | J | L | T | F | G | S | G | T | K | V | I | V | L | P |
| pHDS4/203 | J | K | V | F | A | E | G | T | K | L | I | V | I | P |
| Consensus | J$_{beta}$ | L | Y | F | G | E | G | T | R | L | T | V | L |
| Consensus | J$_H$ | D | Y | W | G | Q | G | T | T | V | T | V | S | S |
| Consensus | J$_{kappa}$ |  | T | F | G | G | G | T | K | L | E | I | K | R |
| Consensus | J$_{lambda}$ | W | V | F | G | G | G | T | K | V | T | V | L | G |

FIGURE 6a

|  |  | 103 |  |  |  |  |  |  |  | 110 |  |  |  |  |  | 117 |
|---|---|---|---|---|---|---|---|---|---|---|---|---|---|---|---|---|
| pHDS4/203 | J | G | F | H | K | V | F | A | E | G | T | K | L | I | V | I |
| pHDS11 | J |  |  | E | Q | Y | F | G | P | G | T | R | L | T | V | L |
| 86T1 | J | G | N | T | L | Y | F | G | E | G | S | R | L | I | V | V |
| Consensus | J$_H$ |  | Y | F | D | Y | W | G | Q | G | T | T | V | T | V | S | S |
| Consensus | J$_{kappa}$ |  |  |  | T | F | G | G | G | T | K | L | E | I | K | R |
| Consensus | J$_{lambda}$ |  |  | W | V | F | G | G | G | T | K | V | T | V | L | G |

FIGURE 6b

HETERODIMERIC T LYMPHOCYTE RECEPTOR

BACKGROUND OF THE INVENTION

The U.S. government has rights in this invention by virtue of Grant No. NIH-5-PO1-CA28900-04, NIH-5-P30-CA14051-13 and the Arthritis Foundation.

REFERENCE TO RELATED APPLICATION

This is a continuation of U.S. Ser. No. 666,988 issued as U.S. Pat. No. 4,873,190 Oct. 10, 1989 entitled "Heterodimeric T Lymphocyte Receptor" filed Oct. 31, 1984 by Haruo Saito, David M. Kranz, Herman N. Eisen, and Susumu Tonegawa, which is a continuation-in-part of co-pending patent application Ser. No. 620,122, filed June 13, 1984, issued as U.S. Pat. No. 4,874,845 Oct. 17, 1989 entitled "Heterodimeric T Lymphocyte Receptor" and a continuation-in-part of U.S. Ser. No. 663,809 entitled "T-Cell Receptor-Specific for Antigen Polypeptides and Related Polynucleotides" filed Oct. 22, 1984 by Mark M. Davis and Stephen M. Hedrick, which is a continuation-in-part of U.S. Ser. No. 585,333 filed Mar. 1, 1984 by Mark M. Davis and Stephen M. Hedrick, now abandoned.

The vertebrate immune system is characterized by its ability to respond to an enormously diverse set of antigenic determinants. This capability is due to the synthesis by the body of a set of glycoproteins whose specificity for a single antigen is determined by a variable sequence of amino acids which binds to the antigen. The glycoproteins, which recognize and bind free antigens, are produced by B cells and are called immunoglobulins (Ig).

Each B cell, or bone marrow-derived lymphocyte, produces antibody specific for only one antigen. It has been theorized that the type of immunoglobulin which is produced by the B cell is generated by a series of gene rearrangements and RNA splicing events that result in polypeptide chains consisting of variable and constant regions. These regions can be subdivided into domains held together by interchain and intrachain disulfide bridges situated at the same relative positions. The characteristic primary and secondary structure is made up of heavy and light chains which begin with a leader peptide of 17-29 residues, followed by a variable (V) region of 94-97 residues, then a joining region of 13-17 residues (J), then a constant region (C). The domains of the constant regions of the immunoglobulins are encoded by separate exons from those for the variable region and do not appear to rearrange during development.

T cells or thymus derived lymphocytes, like B cells, are capable of recognizing a wide range of different antigens. The ability to recognize a given antigen is also fixed in any particular clonal line of T cell. T cells, however, recognize only antigens located on the surfaces of cells in the specific molecular context of self major histocompatability complex (MHC) gene products, not freely circulating antigens. T cell receptors recognize foreign antigens (such as viral antigens) in the molecular context of the T cell host's self-MHC gene products or recognize foreign MHC gene products. Cell surface antigens include tumor cell and viral antigens. The ability to recognize cell-bound antigens is acquired when the T cells differentiate in the host thymus.

Effective antisera and monoclonal antibodies have now been developed which recognize and precipitate clone-specific proteins on the surface of functional T cell clones, hybridomas or T cell tumors. Studies using these antibodies have suggested that the specificity-determining portion of a T cell receptor is a heterodimeric glycoprotein of about 90,000 daltons and consisting of an alpha subunit and a beta subunit held together by an inter-chain disulphide bond(s). Peptide fingerprint analysis of alpha and beta chains from several T-cell lines suggest that both subunits are composed of variable (V) and constant (C) regions.

Three groups of workers have since succeeded in isolating T cell-specific cDNA (complementary DNA) clones of mouse or human origin which are homologous to immunoglobulin genes. S. M. Hedrick, E. A. Nielsen, J. Kevaler, D. I. Cohen, and M. M. Davis, as reported in Nature, 308, 153-158 (1984), using a mouse, antigen specific, MHC-restricted T helper hybridoma TM86, demonstrated that the cDNA encoded a protein composed of an amino-terminal variable and a carboxy-terminal constant region. They also showed that the corresponding genomic DNA sequences had undergone clone-specific somatic rearrangements in various T cell lines.

Y. Yanagi, Y. Yoshikai, K. Leggett, S. P. Clark, I. Aleksander, and T. W. Mak, in Nature, 308, 145-149 (1984), reported the nucleotide sequence of a cDNA clone YT35 derived from the human leukaemic T cell line, MOLT-3. The predicted amino acid sequence encoded by the human cDNA clone of Yanagi et al. is highly homologous in the constant region to the cDNA clone isolated by Hedrick et al.

We recently reported in Nature, 309, 757-762 (1984) the cloning and sequencing of two related but distinct cDNA clones pHDS4/203 and pHDS11 from a functional murine cytolytic T lymphocyte clone, 2C, the teachings of which are incorporated herein. The genes corresponding to these cDNA clones are rearranged and expressed in T cells (and not in other cells that have been examined such as B cells, kidney cells, etc.) and also have significant sequence homologies to immunoglobulin V and C genes. The amino acid sequence encoded by clone pHDS11 corresponds to the same T-cell receptor genes as those isolated by Hedrick et al and Yanagi et al.

A second cDNA clone pHDS4/203 was identified as the gene coding for the alpha chain of the T cell antigen receptor. However, subsequent studies have shown that this clone lacks sequences that correspond to sites for N-linked glycosylation and it has recently been shown that both the alpha and beta chains of the T cell receptor are N-glycosylated. Despite the fact that the four clones: YT35, isolated by Yanagi et al, TM86, isolated by Hedrick et al, and pHDS11 and pHDS4/203, isolated by Saito et al, share several common properties, it is unlikely that the clone pHDS4/203 encodes for the alpha subunit of the T cell receptor protein comprising the beta subunit encoded by the genes YT35, TM86, and pHDS11. These four cDNA clones share the following common properties. They are expressed in T cells but not in B cells. The corresponding genes are rearranged in T cells and not in B cells. In the encoded proteins, there are distinctive regions that, proceeding from amino- to carboxy-terminus, correspond to a signal peptide, two immunoglobulin-like domains, a transmembrane peptide rich in hydrophobic amino acids, and a short cytoplasmic peptide. Their deduced amino acid sequences have low but significant homology to those of immunoglobulin-chains. Each gene is composed of separate V, J and C gene segments. In the cases of YT35 and TM86, the corresponding genes have also been shown to have D segments. Their V, (D), and J segments have characteristic signal sequences for gene rearrangement (heptamer and nonamer separated by either 12 or 23 base pairs).

Due to the substantial homology between the sequences of TM86, YT35 and pHDS11, it is likely that they represent the beta subunit of the T cell receptor.

Due to the absence of N-glycosylation sites on the gene PHDS4/203 Saito et al, it is unlikely that this gene represents the alpha subunit of the T-cell receptor.

It is therefore an object of the present invention to provide a T-cell receptor gene or nucleotide sequence which codes for both subunits of the T-cell receptor.

It is a further object of the present invention to provide murine cDNA clones which code for either the alpha or beta subunit of the T cell receptor.

It is a still further object of the present invention to provide hybridization probes for identifying and isolating the T cell receptor genes and subunits of the T cell receptor genes of other, non-mouse species, including the human specie.

Another object of the present invention is to provide the protein or amino acid sequence of a murine alloreactive cytotoxic T lymptocyte receptor, including both of its subunits.

It is yet another object of the present invention to provide specific antibodies to the T cell receptor and subunits of the T cell receptor which are useful for identification, isolation, and in other methods for which antibodies are useful such as in delivering antibody bound drugs to a specific cell.

SUMMARY OF THE INVENTION

The complete nucleotide and amino acid sequences for the T cell receptor derived from the alloreactive cytotoxic T lymphocyte (CTL) clone 2C, of BALB.B origin and specific for the product of a Class I gene at the D end of the BALB/c H-2 complex (d haplotype) is disclosed. Two related but distinct cDNA clones corresponding to the alpha and beta subunits of the T cell receptor were cloned and sequenced. The genes corresponding to these cDNA are rearranged and expressed in CTL clones but not in myelomas and the rearrangement pattern varies with the CTL clone. The corresponding poly(A)+ RNA is composed of 5'-variable and 3'- constant regions. The encoded subunits are composed of a signal peptide, two immunoglobulin-like domains, each with one disulphide loop, a transmembrane peptide, and a cytoplasmic peptide. The two domains are homologous to variable and constant domains of immunoglobulin chains, particularly those of lambda light chains. Besides having two cysteine residues in each domain, the encoded subunits have a fifth cysteine residue in the region between the disulphide bonded peptide loop of the constant domain and the transmembrane peptide, at a position where the two subunits may be disulphide bonded to each other.

The constant region sequence of the beta subunit as encoded by the gene pHDS11 from a cytotoxic T-cell is compared to the constant region sequence of the beta subunit of a T helper cell and found to correspond. It is therefore concluded that the disclosed T cell specific cDNA sequences for the constant region of at least the beta subunit and probably the alpha subunit may be used to produce protein, and antibody to that protein, which are useful in isolation, identification, and other methods for both cytotoxic T lymphocytes and T helper cells. Expected homology among mammalian species, including man, further extends possible applications of the present invention.

BRIEF DESCRIPTION OF THE DRAWINGS

FIG. 4 is the nucleotide and predicted amino acid sequences of the cDNA clones pHDS58 (FIG. 4a) and pHDS11 (FIG. 4b). The nucleotide sequence was determined by the method of Maxam and Gilbert, described in *Meth. Enzym.* 65, 499–560 (1980), according to the strategy shown in FIG. 3. Numbers given above the amino acid sequence designate amino acid residue positions. The V, J, C, TM (transmembrane) and CY (cytoplasmic) regions are indicated by horizontal arrows although exact boundaries are ambiguous. Cysteine residues thought to be involved in intra-domain or inter-chain disulphide linkages are encircled. The potential N-glycosylation sites (N-X-S or N-X-T) are also indicated.

FIG. 6a is a comparison of the J region amino acid sequences of pHDS58, that of pHDS4/203, as taught in *Nature* 309, 757–762 (1984), and consensus sequences of the T-cell antigen receptor beta-chain, as taught by Gascoigne et al. in *Nature* 310, 387–391 (1984), and immunoglobulin $J_H$, $J_{kappa}$ and $J_{lambda}$, as taught by Kabat et al. in *Sequences of Proteins of Immunological Interest* (NIH, Bethesda (1983). Those residues common between pHDS58 and any one of the other five J segments are boxed and shaded.

FIG. 6b is a comparison of the J region sequence of the amino acid sequence of pHDS4/203, pHDS11, 86T1, and Ig $J_H$, $J_{kappa}$, and $J_{lambda}$ consensus sequences. Those residues common between pHDS4/203 J and any one of the other 5 J regions are boxed in and shaded.

DETAILED DESCRIPTION OF THE PREFERRED EMBODIMENT

Figure 1A:
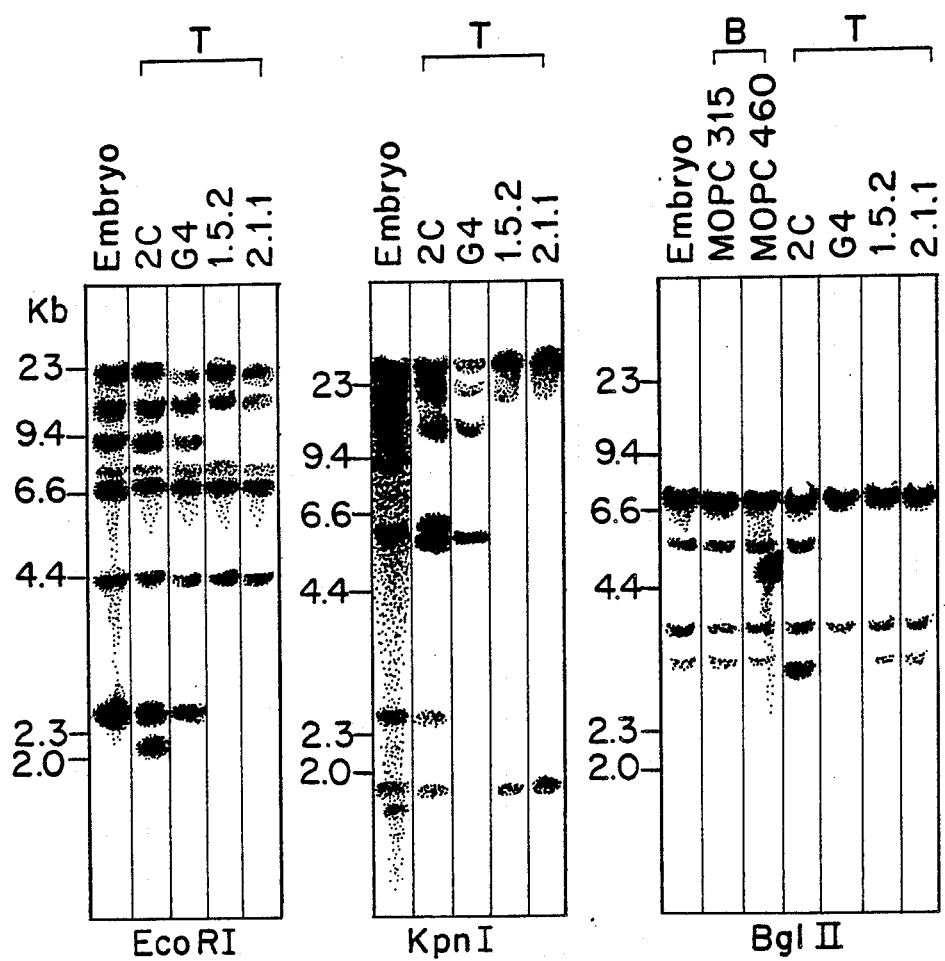
FIG. 1 is a Southern blot analyses, according to the method taught in *Molec. Biol.* 98, 503–517 (1975), of DNA from BALB/c embryo, myelomas MOPC315 and MOPC460, both BALB/c derived, and CTL lines 2C, G4, 1.5.2 and 2.1.1, all BALB.B derived, and described by Kranz et al. in *Proc. Nat. Acad. Sci. USA*, 81, 573–577 (1984). DNA was digested with the indicated restriction enzymes, electrophoresed through 0.8% agarose gels, blotted onto nitrocellulose and hybridized with the $^{32}$p-labelled, nick-translated insert from clone pHDS58 (FIG. 1a) and pHDS11 (FIG. 1b). Hybridization was carried out at 42° C. in 50% formamide and 5×SSC. The filters were washed at 65° C. in 0.2×SSC. Separate experiments showed that BALB/c and BALB.B embryo patterns are indistinguishable. Numbers on the left-hand side are $M_r$ markers.

The preferred embodiment of the present invention is the structure and amino acid and nucleotide sequences of a heterodimeric glycoprotein which functions as a receptor on the surface of a T lymphocyte and comprises both an alpha and a beta subunit. The invention also includes cDNA hybridization probes and antibodies for the identification and isolation of T cell receptors from other species as well as from cytotoxic and helper T cells. The T cell receptor and the nucleotide and amino acid sequences required to produce the protein or its components are defined by their substantial identity to the proposed tertiary structure and nucleotide and amino acid sequences of the receptor of a murine alloreactive cytotoxic T lymphocyte.

The T-cell receptor is made up of two chains, each with two extracellular Ig-like domains, an amino-terminal variable domain, and a carboxy-terminal constant domain. Each of these domains is stabilized by a disulfide bond between cysteine residues that are separated in the linear sequence by 50–70 residues. The alpha chain, consisting of approximately 248 amino acid residues, has cysteine residues at amino acid residues 22, 90 (variable region), 134, 184 (constant region), and 202 (constant region adjacent transmembrane region). The beta chain, consisting of 282 amino acid residues, has cysteine residues at amino acid residues 23, 91 (variable region), 140, 201 (constant region) and 236 (constant region adjacent transmembrane region). The variable region of the alpha subunit, consisting of amino acids 1–98, is joined to the constant region, consisting of amino acids 112 to 222, by amino acids 99–111. The variable region of the beta subunit, consisting of amino acids 1–96, is joined to the constant region, consisting of amino acids 110 to 254, by amino acids 97–109. Beyond the constant domain, each subunit has 8 at its carboxyl-end a peptide carrying an extra cysteine, a hydrophobic stretch of about 20–22 amino acids followed by a short stretch of approximately 5 amino acid residues in which cationic residues abound. These segments correspond, respectively, to the transmembrane and cytoplasmic domains characteristically found in transmembrane proteins.

Figure 4A:
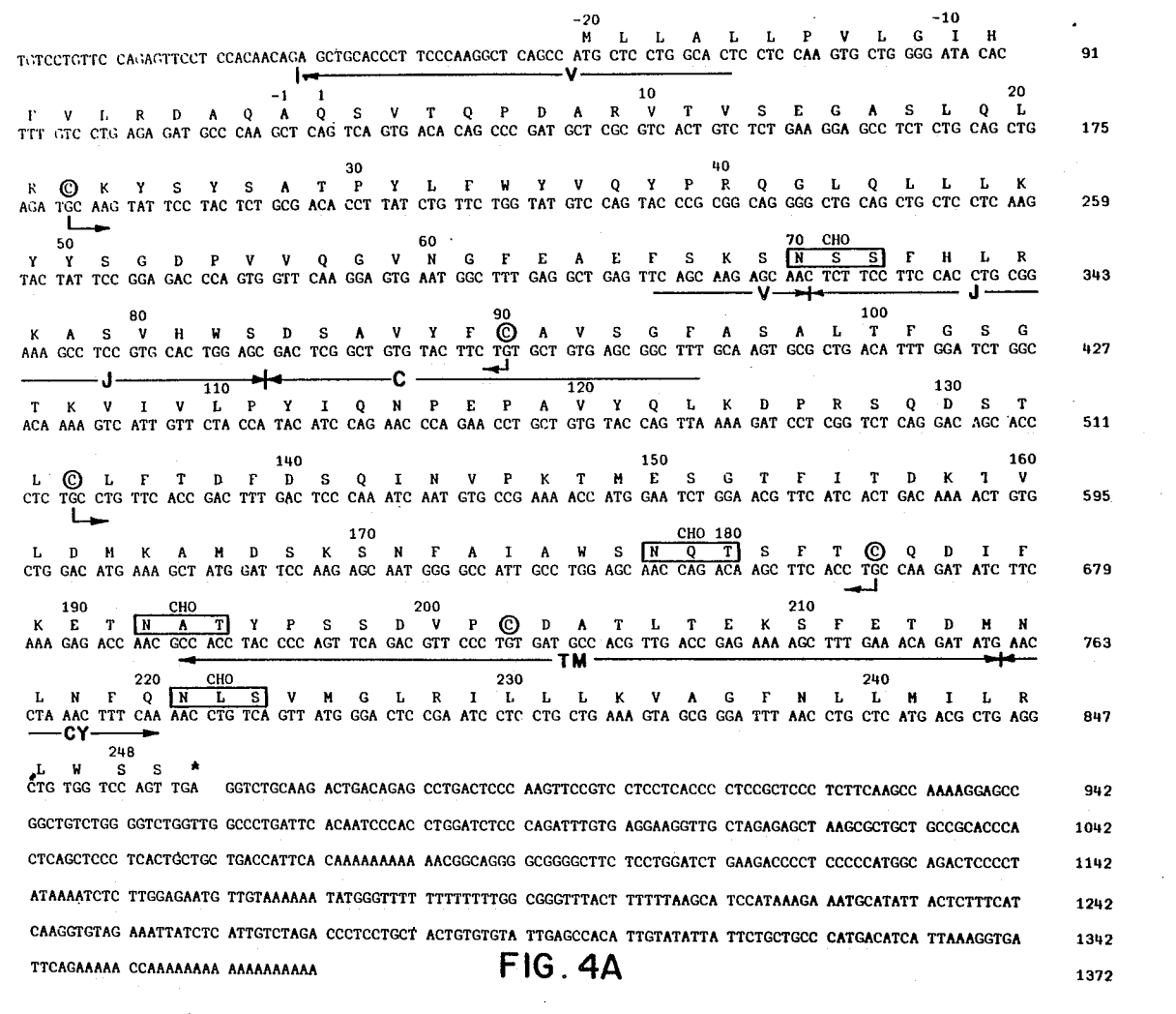
Figure 4B:
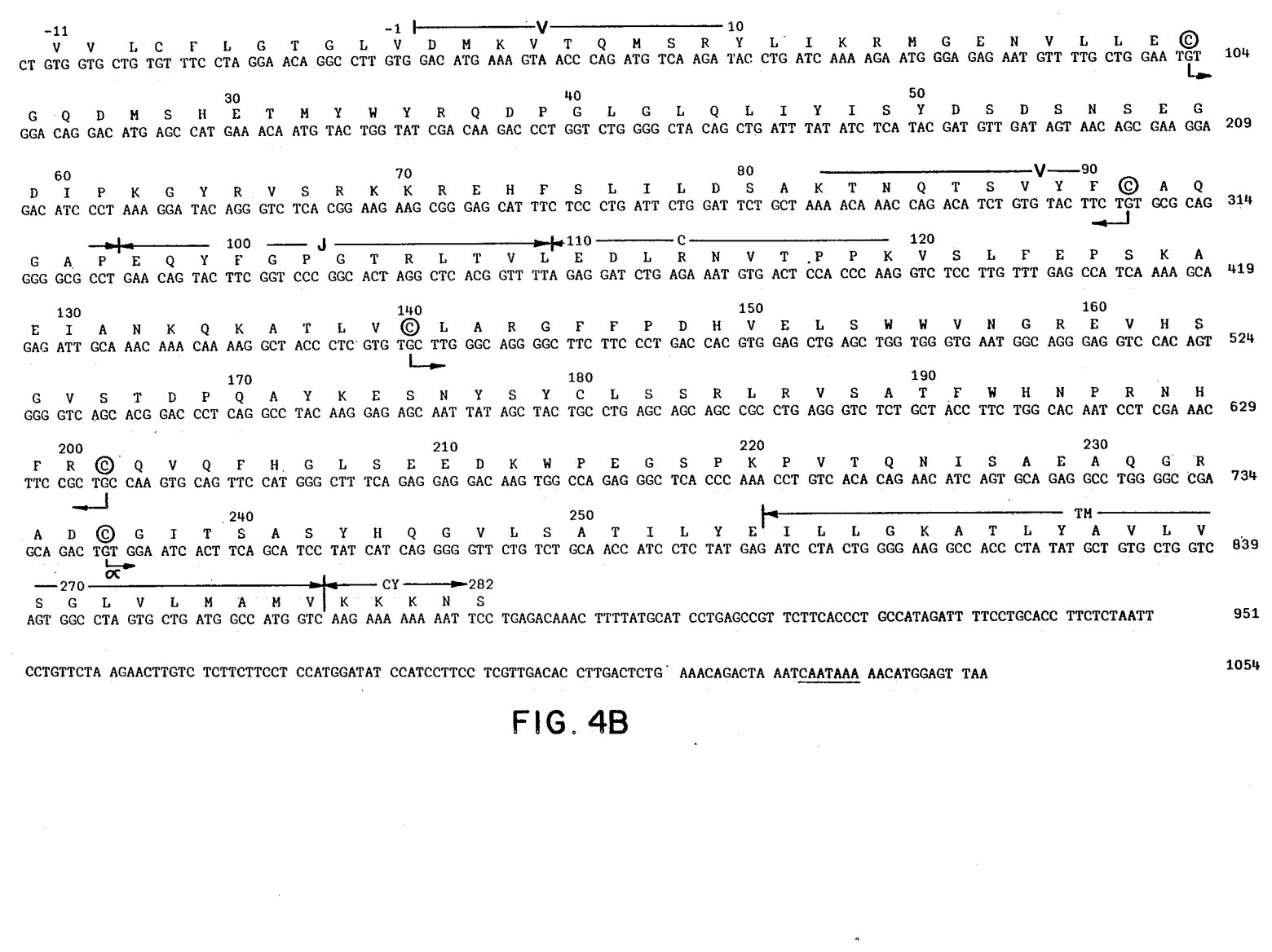

These regions are indicated in FIG. 4a and FIG. 4b by horizontal arrows. The exact boundaries of a few adjacent regions are somewhat uncertain.

The alpha chain, as described, consists of 248 amino acids and has a calculated relative molecular mass of approximately 28,000. The chain contains 23 negatively charged amino acid residues (15 aspartic acid and 8 glutamic acid residues), and 19 positively charged amino acid residues (6 arginine and 13 lysine residues), corresponding to an isoelectric point near neutrality in the absence of post-translation modifications. There are four (4) potential sites for N-glycosylation, represented by the tripeptide Asn-X-Ser/Thr. The potential sites for N-glycosylation are located at amino acid residues 70–72, 178–180, 142–144, and 221–223.

The alpha chain is preceeded by a sequence of 20 amino acid residues. This probably corresponds to a signal peptide, since most immunoglobulin chains carry a signal peptide 19–22 residues long. It has been shown by S. Schlossman that the N-terminal residue of the alpha subunit of the T-cell receptor is blocked, probably by a cyclized glutamine residue. The beta chain is preceeded by a sequence of about a dozen highly hydrophobic residues that also probably comprises part of a signal peptide.

The variable and constant regions of both chains are coded for by distinct gene segments. The same gene appears to code for at least the beta chain constant region of cytotoxic T-lymphocytes and the beta chain constant region of helper T cells. The variable regions of cytotoxic T-lymphocytes (CTL) and helper T cells are probably encoded by non-overlapping gene segments. The apparent homology between the amino acid sequences of constant regions of both helper T cells and cytotoxic T cells enables one to use hybridization probes and antibodies directed against the constant region of the beta chain of the T receptor of either cell type to identify and isolate the T receptor of the other cell type. It is probable that the constant region of the alpha chain is also substantially identical for helper T cells and CTLs.

The invention will be further understood from the following non-limiting example wherein the amino acid and nucleotide sequences and hybridization probes for an alloreactive CTL clone are provided. All of the starting materials for this procedure are readily available to those skilled in the art from commercial or other sources.

Isolation of T cell-specific cDNA clones

T cell-specific cDNA clones were isolated from the alloreactive CTL clone 2C, of BALB.B (mouse) origin and specific for the D end of the BALB/c H-2 complex (d haplotype). This clone was described by D. M. Kranz, D. H. Sherman, M. V. Sitkovsky, M. S. Pasternack, and H. N. Eisen in *Proc. Natl. Acad Sci U.S.A.*, 81, 573-577 (1984).

The cDNA (complementary DNA) synthesized on the poly(A)+ RNA from 2C was substracted twice with poly(A)+ RNA from a mouse B cell lymphoma, A20-2J, according to the method of Hedrick et al. described in *Nature* 308, 149-153 (1984). The B cell lymphoma, described by D. J. McKean, A. J. Infante, A. Nilson, M. Kimoto, C. G. Fathman, E. Walker and N. Warner in *J. Exp. Med.*, 154, 1419-1431 (1981) was used to remove cDNA that cross reacted with B lymphocytes rather than being specific for T lymphocytes. The method of Hedrick et al. is as follows:

(1) $^{32}$p-labelled cDNA is synthesized from cytoplasmic poly(A)+ RNA of a T cell using oligo (dT) and reverse transcriptase;

(2) the RNA template is depleted by base hydrolysis;

(3) the cDNA is hybridized with B-cell mRNA such as B-cell lymphoma line poly(A)+ RNA from Bal 12 or $MBT_H{}^{-B}$; and (4) unbound cDNA is removed by hydroxyapatite chromatography as T-cell specific cDNA.

A library of cDNA from the CTL clone 2C was constructed from the subtracted cDNA using the vector pBR 322 and a standard dC.dG tailing method, such as the one described by T. Maniatis, E. F. Fritsch, J. Sambrook in *Molecular Cloning, A Laboratory Manual*, p. 218, 269-307 (Cold Spring Harbor Laboratory, 1982). The library was screened using two hybridization probes. The first was the 2C cDNA prepared from the poly(A)+ RNA of membrane-bound polysomes followed by subtraction with poly(A)+ RNA from a second B-cell lymphoma, CH1, described by M. A. Lynes, L. L. Lanier, G. F. Babcock, P. J. Wettstein, and G. Haughton in *J. Immunol.*, 121:2352-2357 (1978). The second was the cDNA prepared from the total poly(A)+ RNA from the B-cell lymphoma A20-2J.

After screening about 20,000 independent transformants, a total of 140 putative T-cell-specific cDNA clones were identified and grouped on the basis of the corresponding genes, using the following procedures. First, plasmid DNA preparations from each of 20 randomly chosen cDNA clones were used as hybridization probes in RNA blotting analysis of 2C poly(A)+ RNA and DNA blotting analysis of 2C and embryo DNA. The hybridization patterns allowed assignment of these clones to 12 groups. Second, mouse DNA inserts were dissected from a representative cDNA clone of each group and used as probes for colony hybridization of all of the cDNA clones. This procedure allowed assignment of 105 clones among the 12 groups, as shown in Table 1. The above procedures were repeated for some of the remaining unassigned clones.

TABLE 1

T-cell-specific clones from a subtracted CTL cDNA library

| Group | Size of mRNA (kb) | No. of clones | Rearrangement | Representative clone |
|---|---|---|---|---|
| T(thy1) | 2.0 | 19 | No | pHDS1 |
| B | 0.8 | 19 | No | |
| C(beta) | 1.4 | 18 | Yes | pHDS11 |
| F | 1.7 | 13 | No | |
| E | 0.8 | 12 | No | |
| D | 1.7 | 9 | Yes | pHDS58 |
| K | 1.3/1.1 | 9 | No | |
| G | 1.2 | 8 | No | |
| A | 1.5 | 4 | Yes | pHDS4/203 |
| P | 2.3 | 2 | No | |
| Q | n.d. | 2 | No | |
| I | 2.2 | 1 | No | |
| J | 1.0 | 1 | No | |
| L | 1.5 | 1 | No | |
| N | 4.4 | 1 | No | |
| R | 0.8 | 1 | Maybe | pHDS86 |
| Total | | 120 | | |

The 2C-specific cDNA clones were identified and their plasmid DNA used as hybridization probes in a series of RNA blotting experiments in order to confirm the T cell-specific expression of the corresponding genes. The T cell-specific cDNA were grouped into sets according to the sizes of the corresponding mRNA present in 2C. One probe was found to be for the T cell specific cell surface marker Thy-1 on the basis of its hybridization to a previously identified Thy-1 cDNA clone provided by Mark Davis.

Identification of two distinct classes of T cell-specific cDNA clones whose genes are rearranged in CTL's Representative cDNA clones of each set of T cell-specific cDNA grouped according to its size were used as hybridization probes. Comparison of this cDNA with EcoRI-digested genomic DNA from 2C and BALB.B embryos by the Southern gel blotting method led to identification of three distinct classes of cDNA, represented by clone pHDS11, clones pHDS4 and pHDS203, and clone pHDS58.

FIG. 1a shows the results of Southern gel blotting analysis using clone pHDS58 as the hybridization probe with DNA from BALB/c embryos, four CTL clones of different specificities and two myelomas digested with KpnI, EcoRI, and BG1II restriction enzymes. With each of the three enzymes, the patterns obtained with 2C DNA are different from the patterns obtained with BALB embryo DNA. Clone 2C showed an extra fragment not present in embryo DNA and lacked fragments which were present in embryo DNA. The myeloma DNA patterns are the same as the embryo DNA patterns.

Figure 1B:
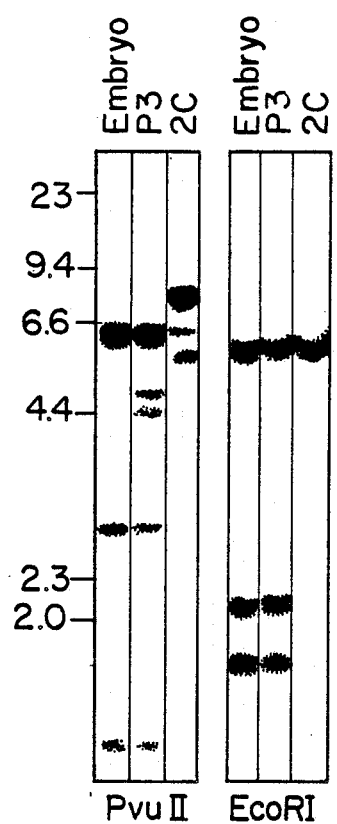

FIG. 1b shows the results of Southern gel blotting analysis using clone pHDS11 as the hybridization probe with DNA from BALB/C embryos, myeloma P3 (BALB/C derived), and CTL 2C (BALB.B) digested with PvuII and EcoRI.

These results strongly suggest that the genes corresponding to clone pHDS58 and clone pHDS11 are rearranged in cytotoxic T cells but not in myelomas and are clearly distinct.

Figures 2A, 2B:
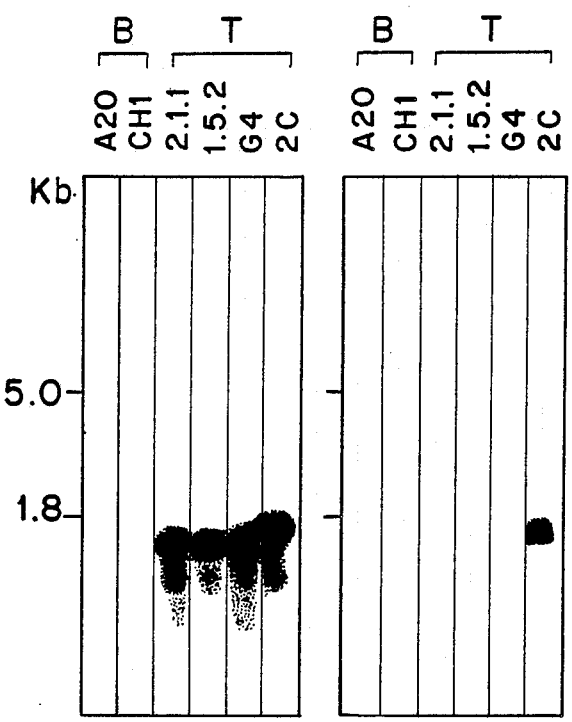
FIG. 2 is a RNA blot analyses, according to the method taught in *Meth. Enzym.* 100, 255–266 (1983), of poly(A)+ RNA from various B- and T-cell lines. Probes: a, total insert of pHDS58; b, HpaII fragment containing 270 bp at the end of the pHDS58 insert (V-region probe); and C, total insert of pHDS11. RNA was extracted from B-cell lymphomas A20-2J and CH1 and alloreactive (H-2$^b$ anti-H-2$^d$) cytotoxic T-lymphocyte clones 2.1.1, 1.5.2, G4 and 2C. Approximately 1.5 microgram of poly(A)+ RNA was denatured with glyoxal and electrophoresed through 1% agarose gel in 10 mM sodium phosphate buffer (pH 6.5). RNA was transferred to nitrocellulose membrane and hybridized to $^{32}$p-labelled nick-translated probe DNAs, as described in FIG. 1. The filter used for hybridization with the first probe was washed by boiling at 100° C. for 5 min in H$_2$O and reused for hybridization with the second probe.
Figure 2C:
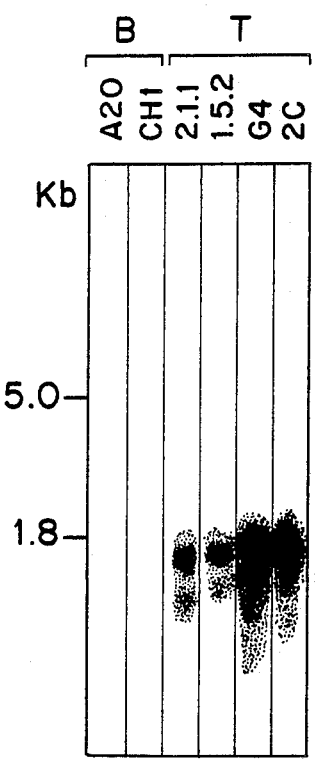

The expression of the pHDS58 gene in CTL clones and B lymphomas was examined by Northern hybridization analyses according to the method of P. S. Thomas in *Meth. Enzym.*, 100, 255-266 (1983). As shown in FIGS. 2a and 2c, when the whole insert of pHDS58 (FIG. 2a) or pHDS11 (FIG. 2c) was used as the hybridization probe, poly(A)+ RNA of distinct sizes was detected in clone 2C and three other independently derived alloreactive CTL clones but not in either of the B lymphomas A20-2J and CH1.

When pHDS58 was used as the hybridization probe, the size of the major RNA species in 2C (1.7 klilobases, kb) was slightly greater than in the other three CTL clones (1.6 kb). Minor RNA species of about 1.2 kb were detected in all four CTL clones.

Figure 3A:
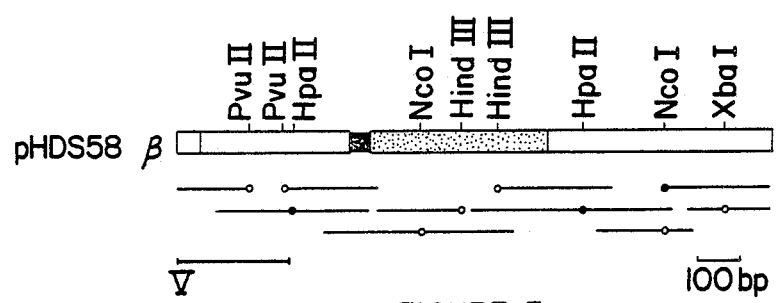
FIG. 3 is a restriction map of the insert of cDNA clones pHDS58 (FIG. 3a) and pHDS11 (FIG. 3b). The map was constructed by a combination of single and double restriction enzyme digestions of the plasmid DNA. The V, J, C and 5'- or 3'-untranslated regions are shown by shading, black, hatching and white, respectively. The sequencing strategy used to determine the nucleotide sequence shown in FIG. 4 is shown. The arrows indicate the directions and the extent of sequence determination. The open and closed circles indicate that the ends of the DNA fragments labelled are 5' and 3', respectively.

When a DNA fragment containing 270 base pairs from the 5' end of the pHDS58 insert was used as the hybridization probe, only the 1.7 kb RNA species of 2C was detected and the other three CTL clones and the B-cell lymphomas exhibited no hybridization, as shown by FIG. 2b. FIG. 3a shows the region of the cDNA sequence covered by the probe. These results suggest that the 1.6-1.7 kb RNA is composed of a common 3' sequence (C region) and a CTL clone-specific 5' sequence (V region), as had been seen with immunoglobulin and the T cell receptor beta chain.

When pHDS11 was used as the hybridization probe, the size of the RNA was somewhat variable from one CTL to another. CTL 2C, 1.5.2, and 2.1.1 all gave a major RNA component of about 1,300 bases while CTL G4 contained two major components of 1,400 and 1,200 bases.

Nucleotide Sequence Analyses

Figure 3B:
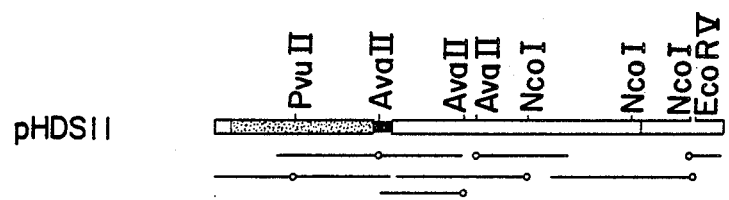

As shown in FIG. 3, restriction maps of the pHDS58 cDNA clone (FIG. 3a) and the pHDS11 cDNA clone (FIG. 3b) were constructed using standard procedures such as the ones described by T. Maniatis, E. F. Fritsch, J. Sambrook in *Molecular Cloning, A Laboratory Manual*, p. 3-54, 374-401 (Cold Spring Harbor Laboratory 1982). The DNA sequence was determined using the method of A. M. Maxam and W. Gilbert in *Methods in Enzymology*, L. Grossman and V. Moldave, Editors, 65:499-560 (Academic Press, N.Y. 1980).

The entire nucleotide sequence of the 1,054 base pair insert of clone pHDS11 is shown in FIG. 4b. The longest open reading frame is composed of an 879 nucleoticle stretch whose corresponding amino acid sequence of 293 residues is also shown in FIG. 4b. The codons are numbered starting with the triplet GAC at nucleotide position 36-38. There is a stretch of about a dozen highly hydrophobic residues at the 5' end of the open reading frame that probably comprise part of a signal peptide. Homology between the pHDS11 protein and immunoglobulin variable regions (V), particularly $V_k$ regions, suggests that Asp at position 1 is the N-terminal residue. The variable region is between codons 1 and 96 and the joining region from codons 97 to 109.

The major body of the constant region is defined by codons 110 (Glu) and 236 (Cys). Codon 236 (Cys) is prior to the N-terminus of the transmembrane segment (TM) which extends from codon 256 to 277. The constant region pHDS11 sequence is identical to the sequence of the corresponding region of the thymocyte cDNA clone, 86T1, described by Hedrick et al., except for one base pair in codon 159.

The sequence identity of the constant region between pHDS11 and 2B4#71 from a cDNA clone isolated from T helper cell ($T_H$) hybridoma specific for anti pigeon cytochrome C is also striking. The $T_H$ cDNA clone is described by Yih Chien, N. R. J. Gascoigne, J. Kevaler, N. E. Lee, and M. M. Davis in *Nature* 309, 322-326 (1984) and *Nature* 310, 387-391 (1984).

The two sequences are identical throughout the constant regions and the entire 3' untranslated region except for two base pair differences at codon 159 and at nucleotide positions 992.

The joining region from codons 97 to 109 in the pHDS11 sequence is distinct from 8671 and 2B4#71, but homologous to the joining segments of Ig genes. As shown in FIG. 6b, the pHDS11 joining sequence corresponds exactly to the sequence of the $J_T7$ genomic segment recently identified and characterized by Chien et al.

The pHDS11 sequence between codons 1 and 96 is quite different from the corresponding region of either 86T1 or 2B4#71. There are areas of conserved residues between the three sequences, however, and between these sequences and the immunoglobulin variable regions of both heavy and light chains, in particular, the two cysteine residues involved in intradomain disulfide linkages and the Trp residue at residue 34.

Another stretch of a highly conserved hydrophobic region of about 22 residues, immediately between the C-terminal five hydrophilic residues and the constant region constitutes a transmembrane (TM) peptide. The five hydrophilic residues are thought to extend into the cytoplasm.

Overall, the gene defined by pHDS11 can encode a processed protein of 282 residues with a relative molecular mass of 33,000 daltons. There are four potential sites for N-glycosylation.

The entire nucleotide sequence of the 1,372 base pair insert of clone pHDS58 is shown in FIG. 4a. The longest open reading frame begins with the Met codon at nucleotide positions 56-58, extends over a stretch of 804 bp, and ends at nucleotide position 859. The corresponding amino acid sequence of 248 residues is also shown in FIG. 4a. The codons and amino acids are numbered starting with the triplet CAG (Gln) at nucleotide positions 116-118. The amino acid sequence imemdiately following the Met and extending to the Gln is highly hydrophobic and probably comprises part of a signal peptide.

After the Gln, the sequence of clone pHDS58 is significantly homologous to that of pHDS11 and the polypeptide chain encoded by pHDS4/203, as well as to the sequences of an immunoglobulin heavy-chain (93G7), an immunoglobulin kappa light chain (MOPC603) and an immunoglobulin lambda 1 light chain (MOPC104E).

Figure 5A:
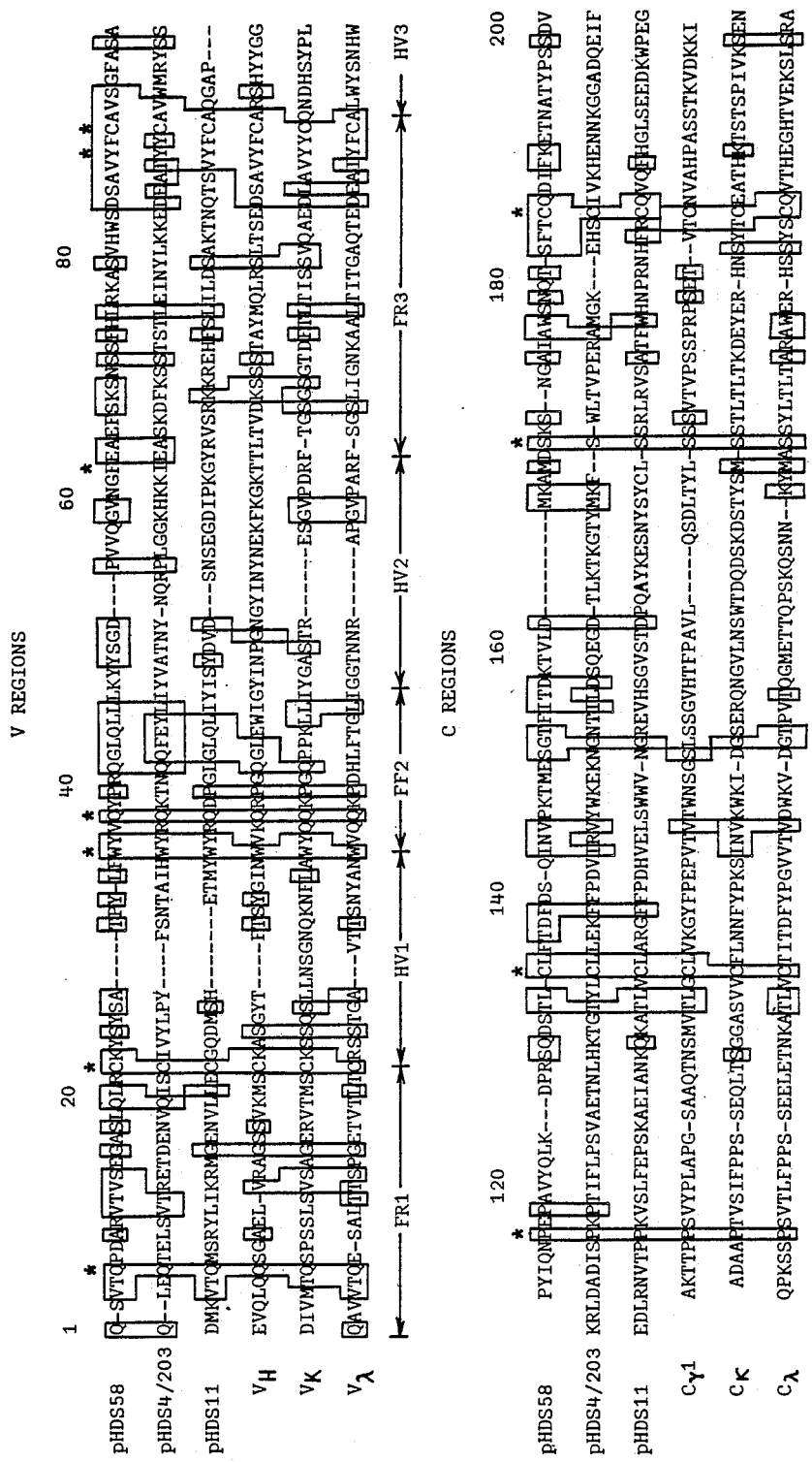
FIG. 5 is a comparison of the V and C regions of the predicted amino acid sequence of pHDS58 and the V and C regions, respectively, of the predicted or determined amino acid sequences of five other polypeptide chains: a chain encoded by pHDS4/203, the beta-chain encoded by pHDS11, 93G7 $_{gamma}$1 immunoglobulin heavy chain, MOPC603 $_{kappa}$ light chain, and MOPC104E $_{lambda}$1 light chain, as taught by Kabat et al. in *Sequences of Proteins of Immunological Interest*, (NIH, Bethesda (1983). Those residues common between the PHDS58 protein and any one of the other five chains are boxed. *, the residues common among all six chains. Approximate boundaries of framework and hypervariable regions as they appear in immunoglobulin V regions are indicated by horizontal arrows. The amino acid positions refer to those of PHDS58 protein.
Figure 5B:
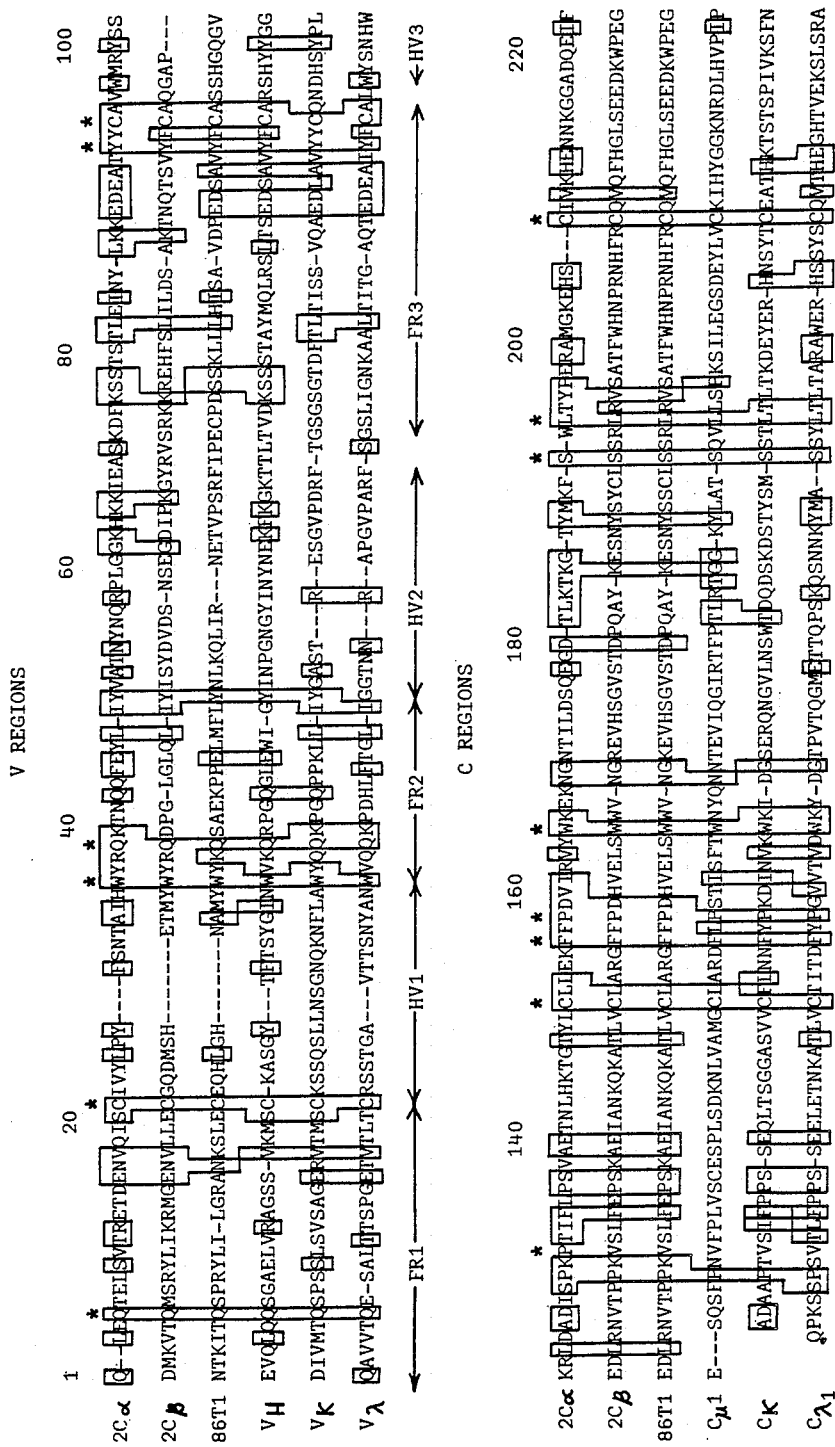

The homology is shown in FIGS. 5a and 6a, where the pHDS58 amino acid sequence is compared with the V (or V+D), J and C region sequences of the other five polypeptide chains. Sequence homology is evident in all three regions, but is most striking in the J region, where it amounts to 38–62%. In the V regions, the pHDS58 sequence is related to the other five sequences by 22–29% homology. The six amino acid residues that are conserved in this region among pHDS11, pHDS4/203 and the three types of immunoglobulin chains (Gln, Cys, Trp, Gln, Tyr and Cys at positions 5, 22, 34, 37, 88 and 90, respectively) are also shared by pHDS58.

The sequence homology is least in the C regions, where it ranges over 12–20%. Nevertheless, the relatedness is evident around the two Cys residues that form intra-domain disulphide bonds in immunoglobulin chains. Throughout the V, J and C regions, the pHDS58 sequence, like the pHDS11 and pHDS4/203 sequences, is more homologous to the light chains (25% and 27% for kappa and lambda respectively) than to the heavy chain (23%).

Beyond the C region, the pHDS58 polypeptide chain exhibits no obvious sequence homology to the corresponding regions of pHDS11 or the chain encoded by pHDS4/203. Nevertheless, the three polypeptide chains are organized in a very similiar fashion in these regions. Thus, as in the pHDS11 and pHDS4/203 chains, the C region of the pHDS58 chain is followed by a peptide carrying an extra cysteine, then by a stretch of about 20 hydrophobic residues that corresponds to a transmembrane peptide and finally by a short hydrophilic C-terminal peptide that presumably extrudes into the intracytoplasmic space.

In FIG. 4a, these regions of pHDS58 are indicated by horizontal arrows. The exact boundaries of a few adjacent regions are somewhat uncertain. For instance, it is not possible to determine unambigiously the N-terminus of the processed protein from the nucleotide sequence of the cDNA alone. However, the Gln at nucleotide positions 116–118 is the best candidate for the following reasons. First, the proposed assignment places the first Cys residue at position 22, while the corresponding Cys residues of most immunoglobulin chains are at positions 22 or 23. Second, most immunoglobulin chains carry a signal peptide of 19–22 residues. The present assignment makes the proposed signal peptide 20 residues long. Finally, the pHDS58 chain is an excellent candidate for the alpha subunit of the T-cell receptor, whose N-terminal residue has recently been shown to be blocked probably by a cyclized glutamine residue by S. Schlossman.

The proposed polypeptide chain is 248 amino acids long. The calculated relative molecular mass is approximately 28,000. The chain contains 23 negatively charged (15 aspartic acid and 8 glutamic acid residues) and 19 positively charged residues (6 arginine and 13 lysine residues), corresponding to an isoelectric point near neutrality in the absence of post-translation modiffcations. As shown in FIG. 4a, it has four potential sites for N-glycosylation. Endoglycosidase F digestion of the alpha/beta heterodimers of mouse helper T cells in a human T-cell tumour by J. P. Allison suggested that both subunits of these T-cell receptors are N-glycosylated. Typical N-glycosylation sites are shown by the tripeptide Asn-X-Ser/Thr. Recent studies have also shown that the alpha subunit of CTL clone 2C is N-glycosylated. As shown in FIG. 4a, the proposed N-glycosylation sites are at amino acid residues 70–72, 178–180, 192–194 and 221–223.

The variable region of the alpha subunit is between amino acids 1 and 98. The major body of the constant region is defined by amino acids 112 (Tyr) and 221 (Asn). A joining region between the variable region and the constant region extends from amino acids 99 to 111. Amino acid 202 (Cys) is prior to the N-terminus of the transmembrane segment (TM) which extends from amino acids 222 to 243.

The joining region from amino acid residues 99 to 111 is homologous to the joining segments of Ig genes. As shown in FIG. 6a, the pHDS58 joining sequence corresponds to the sequences of the T-cell antigen receptor beta-chain described by Gascoigne et al. in *Nature* 310, 387–391 (1984), and immunoglobulin $J_H$, $J_{kappa}$, and $J_{lambda}$ described by Kabat et al. in *Sequences of Proteins of Immunological Interest*, (NIH, Bethesda (1983)).

As shown in FIG. 5a, the pHDS58 sequence between amino acids 1 and 100 (variable region) and amino acids 110 and 200 (constant region) have areas of conserved residues with a chain encoded by pHDS4/203, the beta-chain encoded by pHDS11, 93G7$_{gamma}$1 immunoglobulin heavy chain, MOPC603$_{kappa}$ light chain, and MOPC 104E$_{lambda}$1 light chain.

Another stretch of a highly conserved hydrophobic region of about 20 residues, between the C-terminal five hydrophilic residues and the constant region constitutes a transmembrane (TM) peptide. The five hydrophilic residues are thought to extend into the cytoplasm.

Overall, the gene defined by pHDS58 can encode a processed polypeptide chain of 248 amino acid residues with a relative molecular mass of approximately 28,000 daltons. There are four potential sites for N-glycosylation.

SUMMARY

On the basis of T cell-specific expression, T cell-specific rearrangement, and sequence homology to immunoglobulin chains and to the beta chain purified from Reinherz et al. (personal communication) from a T cell tumor REX and the cDNA clones reported by Hedrick et al. (TM 186) and Yanagi et al. (YT35), pHDS11 has been shown to code for the beta subunit of the mouse T cell receptor.

The gene defined by cDNA clone pHDS58 is expressed and rearranged specifically in T cells. This gene and its product share several characteristics with pHDS11 and pHDS4/203, and their products. These similiarities may be summarized as follows.

1. The genes are specifically expressed in various CTL clones but not in B lymphomas.
2. The genes are rearranged in CTL clones but not in myelomas, and the rearrangement pattern varies with CTL clone.
3. The corresponding poly(A)+ RNA is composed of 5'-variable and 3'-constant regions.
4. The primary sequences suggests that the encoded protein is composed of a signal peptide, two immunoglobulin-like domains, each with one disulphide loop, a transmembrane peptide and a cytoplasmic peptide.
5. The two domains are homologous to the V and C domains of immunoglobulin chains, particularly those of lambda light chains.
6. Besides having two cysteine residues in each domain, the encoded protein has a fifth cysteine residue in the region between the C domain and the transmembrane peptide, at a position where the chain might be dislphide bonded to another chain.

Figure 7:
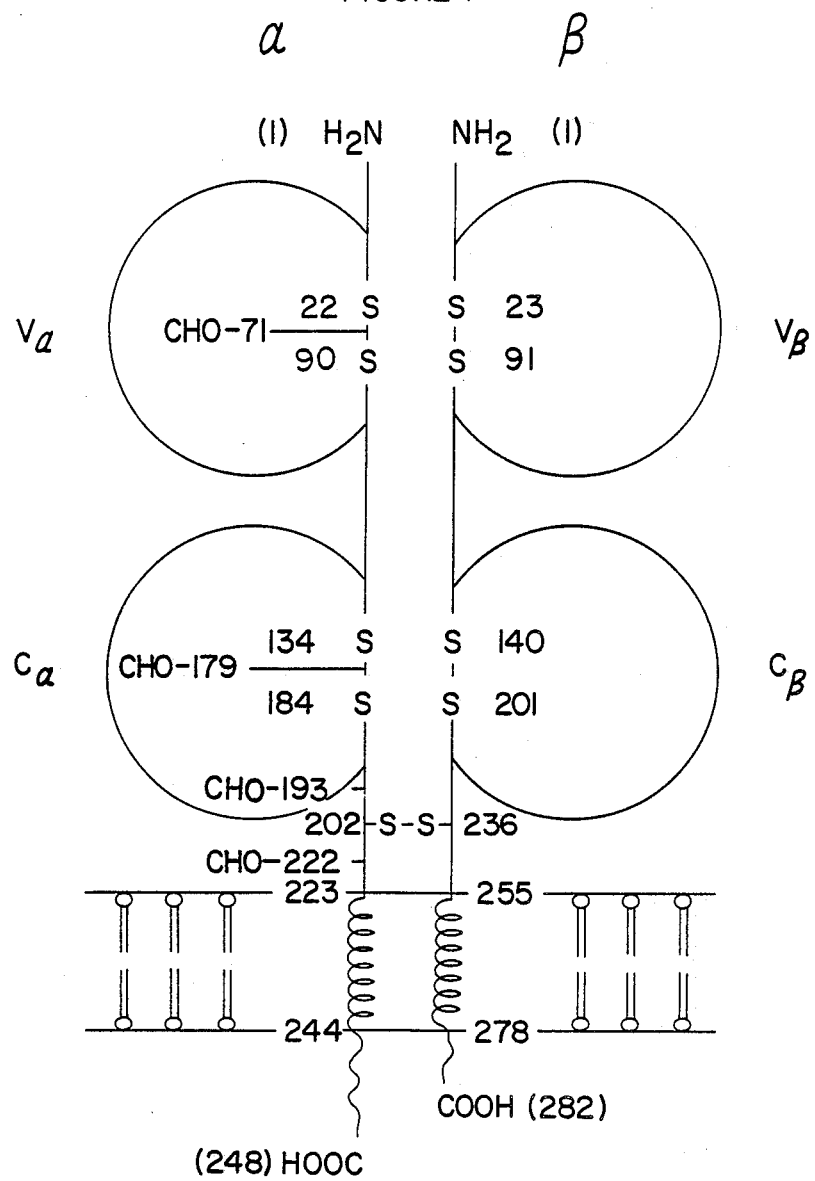
FIG. 7 shows the proposed overall structure of the 2C T-cell receptor. Each receptor molecule is made up of two chains, alpha and beta, each with two extracellular Ig-like domains, an amino-terminal variable and a carboxy-terminal constant domain. Each of these domains is stabilized by an S-S bond between cysteine residues. The two chains are held by a single interchain S-S bond located close to the cell's outer membrane. The protein is anchored on the membrane by two (one for each chain) hydrophobic transmembrane peptides. A short carboxy-terminal peptide rich in cationic residues extends into the cytoplasm in each chain. Both alpha and beta chains are N-glycosylated, with the sites indicated on the alpha subunit by CHO.

The proposed structure for the T cell receptor is shown in FIG. 7. The receptor molecule is made up of two chains, each with extracellular immunoglobulin-like domains, an amino-terminal variable domain and a carboxy-terminal constant domain. Each domain is stabilized by a disulfide bond between cysteine residues that are separated by a linear sequence of 50–70 residues.

Cysteine residues at positions 202 and 236 of the alpha and beta subunits, respectively, form a single, interchain disulfide bond located close to the cell outer membrane. This bond may link the two subunits in the intact molecule and account for the difference in apparent molecular weight between the unreduced and reduced receptor (90,000 daltons versus 40–45,000 daltons) in SDS-polyacrylamide gel electrophoresis. The molecular weights of the alpha and beta subunits are each less by about 10,000 to 15,000 daltons than the apparent molecular weight observed in SDS-polyacrylamide gel electrophoresis. It is possible this difference is due to N-glycosylation of the subunits.

A stable association between the two subunits may be required to form an effective binding region, as is characteristic of immunoglobulins. The obligate participation of two different subunits in the formation of a single combining site means that combinational variability is likely to contribute to structural and functional diversity of these receptors.

The presence of 18–22 hydrophobic amino acids, followed by a short stretch of amino acid residues in which there are many cationic residues, at the carboxyl-end of the constant domain corresponds to the transmembrane and cytoplasmic domains that are characteristically found in transmembrane proteins.

The T cell receptor is defined in the example by its amino acid sequence, nucleotide sequence of variable, joining, constant, transmembrane, and cytoplasmic segments, arrangement of disulfide bonds and glycosylation sites.

Considering the high sequence homology observed between two corresponding genes belonging to two mammalian species (for example, mouse Ig $C_k$ and human Ig $C_k$ are 60% homologous, mouse Ig $C_{lambda}$ and human Ig $C_{lambda}$ are 65% homologous, rabbit $C_{H2}$ and human $C_{H2}$ are 63% homologous, and rabbit $C_{H3}$ and human $C_{H3}$ are 66% homologous (Davis et al, *Microbiology*, 2nd Ed., p. 441 (Harper & Row Publishers, 1973) and comparing homology between the gene sequence of Hedrick et al and Yanagi et al for the beta subunit of the T cell receptor) with that of pHDS11, it is highly probable that the alpha and beta genes of different mammalian species, including human, can be cloned from the T cell cDNA libraries of these species using the disclosed mouse alpha and beta cDNA as hybridization probes.

The cDNA may be used in various systems known to those skilled in the art to make large quantities of the actual T cell receptor protein. This is of tremendous use since a major limitation on previous work was the small amount of T cell receptor available for study. Both procaryotic and eucaryotic systems are useful for production of T cell receptor protein or the alpha or beta subunits of the receptor.

An example of a method of producing protein from the cDNA is taught by copending application U.S. Ser. No. 592,231, to Gillies et al., entitled "Enhanced Production of Proteinaceous Materials in Eucaryotic Cells" and filed Mar. 22, 1984.

Another method is taught by Gray and Goeddel, entitled "Cloning and Expression of Murine Immune Interferon cDNA", *Proc. Natl. Acad. Sci. USA*, 80:5842–5846 (1983).

The eucaryotic system has the advantage over the procaryotic system that the expressed molecule is glycosylated.

The T cell receptor protein or polypeptide sequences may be used for further studies, in systems for the detection of anti-T cell antibodies, and in other procedures known to those skilled in the art. They may also be used for the production of specific T cell receptor antibodies which are directed against the entire molecule, the alpha or beta subunit, or specific regions within the molecule, such as the constant region. The antibodies directed against the constant region of the cytotoxic T lymphocyte should be equally effective against the constant region of T helper cells.

Antibodies may be produced from the protein or its subunits using conventional techniques known to those skilled in the art. Nucleotide sequences may also be utilized to produce short peptides or fusion proteins which are then bound to a carrier protein such as bovine gamma globulin (BTG) for injection into an animal for the production of antibodies. For example, an animal may be immunized against the protein or peptide bound protein and immunoglobulin isolated from the serum. The B cells from the immunized animal with the desired specificity may also be fused with a cell line which is maintained in cell culture, such as myelomas or other tumor cell lines, to form hybridomas for the continuous production of antibody.

Antibodies are useful in isolation procedures such as by affinity chromatography wherein antibody is bound to a solid matrix and by precipitation of soluble antibodies in solution. Antibodies are useful in analysis and identification using any of a number of well known techniques. A recently developed use of antibodies involves binding an agent, such as a drug, to the antibody, then injecting the bound antibody into a patient so that the drug is delivered only to the desired site. In the present invention, an example of such a use would be delivery of a chemotherapeutic compound to malignant T cells in a patient with a T cell lymphoma.

The invention may be embodied in other specific forms without departing from the spirit and scope thereof. These and other modifications of the invention will occur to those skilled in the art. Such other embodiments and modifications are intended to fall within the scope of the appended claims.

What is claimed is:

1. A substantially pure clonally diversified integral membrane protein free of T lymphocyte membrane constituents comprising an alpha subunit and a beta subunit, said protein of mammalian origin functioning as a receptor for antigens and major histocompatibility complex gene products when located on the surface of the T lymphocyte, wherein said subunits comprise:

a signal peptide comprising between 12 and 22 amino acid residues;

a variable, immunoglobulin-like domain having a binding site specific for at least one MHC gene product, wherein said variable domain has a first and second cysteine residue from the N-terminus;

a constant, immunoglobulin-like domain having substantial identity to a corresponding amino acid sequence in receptors of both helper T lymphocytes and cytotoxic T lymphocytes, wherein said constant domain has a third and a fourth cysteine from the N-terminus;

a joining region comprising an amino acid sequence connecting said variable and said constant domains;

a transmembrane peptide comprising a sequence of predominantly hydrophobic amino acids; and a short cytoplasmic peptide comprising a sequence of predominately cationic amino acids;

wherein said said transmembrane peptide is between said constant domain and said cytoplasmic region, and wherein the constant region between said fourth cysteine and said transmembrane peptide has a fifth cysteine residue for formation of a disulphide bond between said alpha subunit and said beta subunit, and wherein each of said subunits contain four sites for N-glycosylation, said sites located at a first site between said first cysteine and said second cysteine, at a second site between said third cysteine and said fourth cysteine, and at a third and fourth site in the region between said fourth cysteine residue and said transmembrane peptide when said protein is produced by an alloreactive cytotoxic T lymphocyte clone 2C of BALB.B origin and specific for the D end of the BALB/c H-2 complex (d haplotype).

2. The glycoprotein of claim 1 wherein said alpha subunit comprises a sequence of 248 amino acid residues, said sequence consisting essentially of a signal peptide comprising approximately 22 amino acid residues, a variable region of approximately 98 amino acid residues, wherein the first amino acid is glutamine, and wherein the 22nd and 90th amino acid residues from said first glutamine are cysteine, a joining region of approximately 13 amino acid residues between said variable region and a constant region of approximately 110 amino acid residues, wherein the 134th, 184th, and 202nd amino acid residues from said first glutamine are cysteine, a transmembrane region of approximately 20 to 22 predominately hydrophobic amino acid residues, and a short cytoplasmic region of approximately 5 predominately cationic amino acids; and wherein said beta subunit comprises a sequence of 282 amino acid residues, said sequence consisting essentially of a signal peptide comprising 12 predominantly hydrophobic amino acid residues a variable region of approximately 109 amino acid residues, wherein the first amino acid is asparagine, and wherein the 23rd and 91st amino acid residues are cysteine, a joining region of approximately 13 amino acid residues between said variable region and a constant region of approximately 145 amino acid residues, wherein the 140th, 201st, and 236th amino acid residues are cysteine, a transmembrane region of approximately 22 predominately hydrophobic amino acid residues, and a cytoplasmic region of approximately five predominately cationic amino acid residues; and wherein said alpha and beta subunits are joined by a disulfide bond between cysteine residues at positions 202 from the N-terminus of said alpha subunit and position 236 from the N-terminus of said beta subunit.

3. A substantially pure clonally diversified T lymphocyte receptor protein comprising an alpha subunit and a beta subunit.

* * * * *

UNITED STATES PATENT AND TRADEMARK OFFICE
CERTIFICATE OF CORRECTION

PATENT NO. : 4,970,296
DATED : November 13, 1990
INVENTOR(S) : Haruo Saito, David M. Kranz, Herman N. Eisen, Susumu Tonegawa, Mark M. Davis, Stephen M. Hedrick It is certified that error appears in the above-identified patent and that said Letters Patent is hereby corrected as shown below:

Title Page, Assignees: Replace "Instiute" with -- Institute --

Title Page, Abstract, line 10: Replace "CDNA" with "cDNA"

Col. 3, line 26: Replace "lymptocyte" with "lymphocyte"

Col. 6, line 14: Delete "8"

Col. 9, line 7: Replace "Klilobases" with -- kilobases --

Col. 10, line 39: Replace "imemdiately" with "immediately"

Col. 11, line 5: Replace "similiar" with "similar"

Col. 11, line 36: Replace "modiffcations" with "modifications"

Col. 14, line 56: Delete "said"

Signed and Sealed this

First Day of November, 1994

Attest:

BRUCE LEHMAN

Attesting Officer

Commissioner of Patents and Trademarks